United States Patent [19]

Patell

[11] Patent Number: 4,775,536
[45] Date of Patent: Oct. 4, 1988

[54] ENTERIC COATED TABLET AND PROCESS FOR MAKING

[75] Inventor: Mahesh K. Patell, Edison, N.J.

[73] Assignee: Bristol-Myers Company, New York, N.Y.

[21] Appl. No.: 832,839

[22] Filed: Feb. 24, 1986

[51] Int. Cl.⁴ ............................................. A61K 9/24
[52] U.S. Cl. .................................. 424/471; 424/480; 424/482; 427/3
[58] Field of Search .................. 427/3; 424/482, 471, 424/480

[56] References Cited

U.S. PATENT DOCUMENTS

| | | | |
|---|---|---|---|
| 2,714,084 | 7/1955 | Hermelin | 424/471 |
| 2,991,226 | 7/1961 | Millar et al. | 424/471 |
| 3,431,338 | 3/1969 | Munzel | 424/480 |
| 3,524,756 | 8/1970 | Signorino et al. | 424/471 X |
| 3,909,444 | 9/1975 | Anderson et al. | 427/3 X |
| 4,001,390 | 1/1977 | Ohno et al. | 424/480 |
| 4,176,175 | 11/1979 | Maekawa et al. | 424/480 |
| 4,287,221 | 9/1981 | Tonedachi et al. | 427/3 |
| 4,302,440 | 11/1981 | John et al. | 424/35 |
| 4,432,966 | 2/1984 | Zeitoun et al. | 424/482 X |
| 4,533,562 | 8/1985 | Ikegami et al. | 427/3 |
| 4,681,755 | 7/1987 | Colombo et al. | 424/487 X |
| 4,693,896 | 9/1987 | Wheatley et al. | 424/480 |

FOREIGN PATENT DOCUMENTS

| | | | |
|---|---|---|---|
| 0250665 | 5/1963 | Australia | 427/3 |
| 1178853 | 12/1984 | Canada | 427/3 |
| 58-109413 | 6/1983 | Japan | 427/3 |

*Primary Examiner*—Thurman K. Page
*Attorney, Agent, or Firm*—Morton S. Simon

[57] ABSTRACT

An enteric coated tablet and process is described in which a core tablet of a pharmaceutically active ingredient is provided with an enteric coating layer of a film forming enteric polymer and an overcoat layer of non-enteric film forming polymer; optionally, the tablet may also be provided with the non-enteric undercoat layer of a film forming polymer.

16 Claims, No Drawings

ENTERIC COATED TABLET AND PROCESS FOR MAKING

This invention relates to enteric coated tablets and more particularly to enteric coated aspirin tablets as well as to a process for preparing such tablets. Enteric coating of tablets and especially aspirin tablets, is undertaken to prevent gastric irritation in individuals which often follows the administration of such tablets which are uncoated. Enteric coated tablets resist the action of the acidic stomach fluids and pass through it before the coating can dissolve thus protecting the gastric mucosa from the irritating effects of the ingredients in the tablets e.g. aspirin. However, this coating dissolves in the neutral or alkaline milieu of the intestine and the active ingredients become available for absorption into the blood stream.

Conventionally, enteric coatings have been applied to tablets from solutions of film resins in which the solvents for such solutions are organic solvents. This has complicated the process and introduced many problems. In the first place the organic solvents employed are difficult to work with and often hazardous and require special handling and equipment. Furthermore, the organic solvents are more costly and consequently add to the cost of the final product. Moreover, the use of such solvents introduced problems with respect to environmental protection and the need to comply with more cumbersome E.P.A. regulations. There is also a concern about the toxicity potential of the traces of the residual solvents in the tablet coating that is applied by using organic solvents.

Aside from the above it has ascertained that by-and-large the enteric coated aspirin products on the market failed to meet the USP test standards for enteric aspirin tablets. As will be pointed out in more detail below applicants have tested at least seven commercial enteric coated aspirin products and have found that they fail the USP test for such products. As far as applicant can ascertain these products were prepared by enteric coating the tablets with an enteric coating material using an organic solvent system.

Applicants have found that they can obtain enteric coated tablet products, and particularly aspirin tablets, that consistently pass the USP test for enteric tablets if they apply an enteric coating composition comprising preferably, a water soluble or water solubilized film forming enteric polymer in an aqueous vehicle, allowing it to dry to deposit a layer of enteric coating material on the tablet surface and then applying as an overcoat a further layer of a film forming non-enteric polymer also preferably from an aqueous medium. In the preferred practice of this invention before applying said enteric coating layer to the tablets, an undercoat of a non-enteric film forming polymer is first applied from an aqueous medium and then allowed to dry. This is followed by the application of an intermediate layer of enteric coated film forming polymer and finally by said overcoat of non-enteric film forming resin. The undercoat and the overcoat layers are preferably formed from water soluble or water dispersible non-enteric film forming polymers which are laid down on the tablets from the aqueous vehicles.

In the practice of the present invention the enteric coating solution used to form the enteric coating layer on the tablets will comprise a water soluble or water dispersible film forming enteric polymer dissolved or dispersed in an aqueous vehicle. A number of such film forming enteric polymers are known in the prior art which will serve the present purposes. These will have conventional solubility characteristics of enteric polymers i.e. they will be insoluble in acid but will be soluble in a neutral-to-nearly alkaline medium.

One class of enteric polymers that are eminently suitable for the purpose of this invention are the water soluble or water dispersible acrylic resins. Of special interest in this regard is a polymer sold under the trade name EUDRAGIT L30D. This is a copolymer that is anionic in character and based on polymethacrylic acid and acrylic acid esters. This is described by the formula:

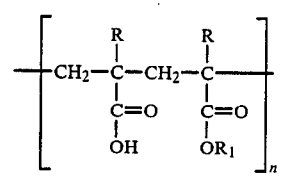

wherein:
n is a number,
R is H or $CH_3$ and
$R_1$ is $CH_3$ or $C_2H_5$,
the ratio of free carboxyl group to ester groups is 1:1 and the mean molecular weight of the polymer is about 250,000.

The coating solution used to prepare the enteric coating layer on the tablets according to this invention may contain the enteric polymer over a range of concentrations. In general this will amount to about 5% to about 15% by weight of enteric polymer based on the total weight of the coating solution with the preferred range being from about 9% to about 12% on the same weight basis. A special advantage of aqueous synthetic polymer dispersions employed in this invention is that the water is merely a dispersing agent and not a solvent for the polymer. This means that water is not retained by the lacquer substance during the formation of the film but evaporates rapidly and almost completely. This aspect is extremely important especially for coating drugs that are highly moisture sensitive such as aspirin.

The undercoat and overcoat layer of the tablets of this invention may be formed from the same or a different film-forming water soluble or water dispersible non-enteric polymers. Many polymers of this type are known in the prior art that may serve the present purposes. By way of illustrating the polymers of this character that may be employed herein mention may be made of the following:
hydroxypropylmethylcellulose
polyvinyl pyrrolidone
hydroxypropyl cellulose
polyethylene glycol 3350, 4500, 8000
methyl cellulose
pseudo ethylcellulose One such polymer that has been found to be very suitable is hydroxypropyl methylcellulose which is a propylene glycol ether of methylcellulose. This is available from several manufacturers as for example from Dow under the trade names HPM Cellulose.

The solutions which will be used to prepare the overcoat or undercoat layers of the present tablets may also vary as to concentration of the non-enteric film forming polymer. Usually the latter will constitute from about 2% to about 8% by weight of said non-enteric film forming polymer based on the total weight of the coating solution with the preferred concentration being from about 5% to about 6% of said non-enteric film former on the same weight basis.

Aside from the enteric or non-enteric film formers the above described coating solution may also contain other ingredients which may aid in the application of the coating material to the tablet or to improve the character of the coating. These may be such ingredients as surfactants, plasticizers, antifoaming agents, solubilizing agents, coloring agents. Usually in all of the solutions utilized the principal liquid vehicle will be water.

The overcoat layer used in the present invention, in addition to contributing to the ability of the tablets of this invention to pass the USP test for enteric coatings has still a further important function. The USP standards for enteric coated tablets also entails stability testing of the products at elevated temperatures for extended periods of time. Tablets that are not provided with the non-enteric overcoat layer in accordance with this invention tend to stick together when subjected to the elevated temperatures that these tests require. Overcoating with the non-enteric polymer as prescribed herein prevents such sticking. Providing an overcoat layer as recommended also has the advantage of giving flexibility in preparing the products in different colors.

For a batch of tablet cores of about 11,000 grams overall weight, the following amounts of coating material solutions can be suitably employed:

| | |
|---|---|
| Solution I - Precoat | 400–3000 g |
| Solution II - Enteric Coat | 3000–7000 g |
| Solution III - Color Coat | 500–4000 g |

The quantitative relationship between the various layers in the finished tablet to the total weight of the tablet, can suitably be as follows:

| | mg/tablet | % total tablet |
|---|---|---|
| Tablet Core weight | 600.000 | 88.2991 |
| After pre coat — tablet weight | 612.000 (Range 603–618) | 90.0652 |
| After pre coat + Enteric coat + talc — tablet weight | 659.652 (Range 640.59–669.18) | 97.0778 |
| After final color coat — tablet weight | 679.441 (Range 666.24–686.04) | 99.9900 |
| Finished tablet weight — after polishing step. | 679.509 | 100.000 |

The following Examples are given to further illustrate this invention. It is understood, however, that the invention is not limited thereto.

The chemical designation of the materials used in the following Example that are identified by trade names are as follows:

| | |
|---|---|
| Avicel pH 101: | Microcrystalline cellulose pH 101 |
| Syloid 244 FD: | Colloidal Silicon Dioxide |
| Povidone: | Polyvinyl Pyrrolidone |
| Tween 20: | Polysorbate 20-Sorbitan monooleate |
| Medical Antifoam AF Emulsion: | Polydimethyl Siloxane and Silicon dioxide |
| Eudragit L30D: | Methacrylic acid ester |
| StaRx starch 1500: | Modified compressible corn starch comprising 5% free amylose, 15% amylopectin and 80% unmodified starch; cold water solubles, % |

-continued

| |
|---|
| d.s.b) 10–20. |

EXAMPLE 1

Aspirin tablet core formulation:

| Ingredients | mg/tablet |
|---|---|
| aspirin 40 mesh | 500.00 |
| Avicel pH 101 | 50.00 |
| StaRx starch 1500 | 48.20 |
| sodium lauryl sulfate | 1.20 |
| Syloid 244 FP | 0.60 |
| Total Tablet Weight | 600.00 mg |

STEP I-UNDERCOAT

The undercoat gives strength to the tablet cores and prepares the tablets for enteric coating.

Approximately 2% film coating solids are applied to the aspirin tablet cores using the following film coating solution and processing steps. This solution contains 12.5% solids.

| Ingredients | % W/W |
|---|---|
| water, deionized | 84.00 |
| hydroxypropyl methyl cellulose | 5.34 |
| Povidone | 1.00 |
| sorbitan monolaurate | 0.75 |
| propylene glycol | 1.20 |
| mineral oil light | 0.20 |
| Tween 20 (Surfactant) | 0.50 |
| Medical Antifoam AF Emulsion | 0.01 |
| color concentrate | 7.00 |
| Total Weight | 100.00 |

Preparation of Undercoat Solution

Heat water to boiling. Add antifoam and the polymer blend. Disperse/dissolve completely. Turn off heat. Start cooling. Mix remaining ingredients together and add to the main coating solution. Mix well.

The film coating solution should be prepared at least 12 hours before use.

Application of Undercoat to Aspirin Tablet Cores

About 11 kilograms of aspirin tablet cores are placed in a coating pan. The tablet cores are agitated in the coating pan and the undercoating solution is sprayed on at the rate of 40 grams/minutes. The temperature is set at 60°–70° C. and the coating time is about 45 minutes.

STEP II-ENTERIC COAT

Approximately 7.25% enteric coating solids are applied onto the tablet cores of Step I using the following enteric coating solution. Solution contains 15.5345% solids.

| Ingredients | |
|---|---|
| Eudragit L30D (30% aq. dispersion) | 2000.00 |
| water, deionized | 3330.00 |
| triethyl citrate | 130.00 |
| propylene glycol | 50.00 |
| Medical Antifoam AF Emulsion | 20.00 |
| mineral oil light | 10.00 |
| sorbitan monolaurate | 40.00 |
| Tween 20 | 20.00 |

| Ingredients | |
|---|---|
| Total Weight: | 5600.00 g |

Preparation of Enteric Coating Solution

All the above ingredients excepting the Eudragit L30D (30% aqueous dispersion) are thoroughly mixed at very high speeds to breakup all the lumps. The Eudragit L30D is then added to this blend and mixed thoroughly, but generally, without very high agitation. At this time 5133.37 g of the enteric coating solution is sprayed onto 11 kg of the undercoated aspirin tablet cores. The spray rate was 30 mg/minute of enteric coating solution, the temperature was set at 70° C.–75° C. and the spray time was 3.5 hours.

On completion of Step II, the exhaust is turned off and 0.5% talcum powder is sprinkled on the tablets.

STEP III-OVERCOAT

Approximately 3% film coating solids are applied to the tablet surface using the same film coating solution as described in Step I and applied in a similar manner.

STEP IV-POLISHING

The color coated tablets from Step III are polished in the coating pan with exhaust turned off by sprinkling 0.01% powdered polishing wax onto the surface of the tablet bed while rotating slowly.

The tablets are rolled in the coating pan until they start to slide. The exhaust is then turned on to remove the excess wax.

These finished enteric film coated tablets have approximately 12.5% total film coating solids applied.

Application of Step III coating prevents tablets from sticking to each other when stress tested at high temperature. It also gives flexibility when preparing this product in different colors.

EXAMPLE 2

A tablet, having a total weight of 679.44 mg in accordance with the present invention is prepared from the following formulations:

| I. Tablet core | mg/tab |
|---|---|
| aspirin (40 mesh) | 500 |
| starch 1500 | 48.2 |
| sodium lauryl sulfate | 1.2 |
| colloidal silica (Syloid 244 FP) | 0.6 |
| Avicel pH 101 | 50.0 |

Tablet cores are precoated with the following formulation:

| II. Pre-coat | mg/tab. |
|---|---|
| water, deionized | 80.64 |
| hydroxypropyl methylcellulose | 5.13 |
| Povidone K2932 | 0.96 |
| sorbitan monolaurate | 0.72 |
| propylene glycol | 1.15 |
| mineral oil, light | 0.19 |
| Tween 20 | 0.48 |
| medical anti-foam AF emulsion | 0.01 |
| color concentrate | 3.36 |

Precoated cores are enteric coated with the following formulation:

| III. Enteric coat | mg/tab. |
|---|---|
| Eudragit L30D (30%) | 30.6 |
| water, deionized | 50.9 |
| triethyl citrate | 6.6 |
| propylene glycol | 2.5 |
| medical anti-foam AF emulsion | 1.0 |
| mineral oil, light | 0.5 |
| sorbitan monolaurate | 2.0 |
| Tween 20 | 1.0 |
| color concentrate | 5.5 |

Next, the enteric coated tablet is finish coated with the following formulation:

| IV. Finish coat | mg/tab. |
|---|---|
| hydroxypropylmethycellulose | 8.45 |
| Povidone K2932 | 1.58 |
| sorbitan monolaurate | 1.19 |
| propylene glycol | 1.90 |
| mineral oil, light | 0.32 |
| Tween 20 | 0.79 |
| medical anti-foam AF emulsion | 0.02 |
| solar concentrate | 5.54 |
| water, deionized | 132.94 |

The finish coated tablets are then polished with carnauba wax powder.

The finished aspirin tablets of Example 2 present invention were compared with seven commercial enteric coated aspirin tablets to evaluate their performance in the USP enteric test. The proposed USP tests for enteric tablets requires that the product withstand agitation (basket at 100 rpm) in the artificial gastric fluid at 37° C., releasing less than 10% aspirin (gastric test) for 2 hours, while dissolving not less than 85% aspirin in 90 minutes in the artificial intestinal fluid at 37° C. with a buffer of pH 6.8. (Intestinal test).

The results of these tests are summarized in the following table. None of the commercial products were stress tested before determining whether they met the USP enteric test because they had failed the USP test even before a stress test would have been made. The 500 mg aspirin product of Example 2 was enteric tested without stress and reported as item 8 of the table. Items 9 and 10 of the table report the resuls of the enteric tests an 500 mg aspirin tablets of Example 2, which has been stressed before the USP enteric test, the tablets of item 9 having been stored for 3 days at a temperature of 60° C. and a relative humidity of 60% and the tablets of item 10 having been stored for 6 days at 60° C. and a relative humidity of 60% in open petri dish before the enteric test. In the case of item 11 the 500 mg aspirin tablets of Example 2 were stored for 6 days at 60° C. in a glass jar with screw cap (dry heat), before being subjected to the enteric test.

In the table commercial products were enteric coated with cellulose acetate phthalate or hydroxypropyl methylcellulose phthalate. These polymers are normally applied to the tablets in this art using an organic solvent system.

As will be seen from the foregoing table all the commercial products that were tested failed the USP enteric test. Enteric coated tablets of this invention made according to Example 2, not only pass this USP enteric test initially, but even after these tablets were stress tested for three and six days at 60° C./60% RH in an open petri dish and for six days at 60° C. in a glass jar with screw cap. In addition, the effect of the stress conditions on the dissolution time at pH 6.8 (intestinal phase) is so slight to conclude that these enteric coated tablets are uneffected by stress storage conditions.

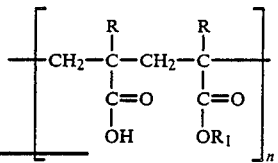

| PRODUCT | GASTRIC TEST (10% released in 2 hours) | INTESTINAL TEST (80% released* in 45 minutes) | RESULT |
|---|---|---|---|
| 1. Commercial Prod. A 325 mg. Tabs (325 mg. Aspirin) | 1–9% | 32–86% | fails |
| 2. Commercial Prod. B 650 mg. Tabs (650 mg. Aspirin) | 0–40% | 63–82% | fails |
| 3. Commercial Prod. C (500 mg. Aspirin) | 1% | 26–60%** | fails |
| 4. Commercial Prod. D (648 mg. Aspirin) | 1% | 5% | fails |
| 5. Commercial Prod. E (500 mg. Aspirin) | 7–8% | 42% | fails |
| 6. Commercial Prod. F (325 mg. Aspirin) | 8% | 40% | fails |
| 7. Commercial Prod. G (500 mg. aspirin) | 0% | 6% | fails |
| 8. tablets of Example 2, | 1% | 85** | pass |
| 9. tablets of Example 2, 60° C./60% RH (open petri dish) | 1% | 85** | pass |
| 10. tablets of Example 2, 6 days at 60° C./60% RH (open petri dish) | 1% | 85** | pass |
| 11. tablets of Example 2, 6 days at 60° C. (Glass jar with screw cap - dry heat) | 1% | 85** | pass |

*USP has revised time period in the intestinal test to a maximum of 90 minutes; with not less than 85% aspirin released.
**these tablets are tested for 45 to 90 minutes.

What is claimed is:

1. An enteric coated tablet comprising a tablet core containing aspirin as an active ingredient, an enteric coat layer encompassing said tablet core, and an overcoat layer encompassing said enteric coat layer, said enteric coat layer comprising a water soluble or water dispersible enteric film forming polymer and said overcoat layer comprising a non-enteric water soluble or water dispersible film forming polymer, said tablet also being provided with an undercoat layer disposed beneath said enteric coat layer, said undercoat layer also comprising a non-enteric water soluble or water dispersible film forming polymer.

2. An enteric coated tablet according to claim 1 wherein said tablet can withstand agitation in a basket at 100 rpm in artificial gastric juice having a pH of 1.2 at a temperature of 37° C. releasing less than 10% aspirin in two hours while dissolving not less than 85% aspirin in 90 minutes in artificial intestinal fluid having a pH of 6.8 at a temperature of 37° C.

3. An enteric coated tablet according to claim 2 wherein said the water soluble or water dispersible film forming enteric polymer is an acrylic resin.

4. An enteric coated tablet according to claim 3 wherein said water soluble or water dispersible film forming enteric polymer is a copolymer that is anionic in character and based on polymethylacrylic acid and acrylic acid esters.

5. An enteric coated tablet according to claim 4 wherein said film forming enteric polymer is of the formula wherein n is a whole number,
R is H or $CH_3$, and $R_1$ is $CH_3$ or $CH_2H_5$—, the ratio of free carboxyl groups to ester groups being about 1:1 and the mean molecular weight of said polymer being about 250,000.

6. An enteric coated tablet according to claim 3 wherein the said water soluble or water dispersible non-enteric polymers of said overcoat layer and said undercoat layer are the same or different and is one of the following polymers:
hydroxypropylmethylcellulose, polyvinylpyrrolidone, hydroxypropylcellulose, polyethyleneglycol, methylcellulose, or pseudoethylcellulose.

7. An enteric coated tablet according to claim 4 wherein the said water soluble or water dispersible non-enteric polymers of said overcoat layer and said undercoat layer are the same or different and is one of the following polymers:
hydroxypropylmethylcellulose, polyvinylpyrrolidone, hydroxypropylcellulose, polyethyleneglycol, methylcellulose, or pseudoethylcellulose.

8. An enteric coated tablet according to claim 5 wherein the said water soluble or water dispersible, non-enteric polymers of said overcoat layer and said undercoat layer are the same or different is one of the following polymers:
hydroxypropylmethylcellulose, polyvinylpyrrolidone, hydroxypropylcellulose, polyethyleneglycol, methylcellulose, or pseudoethylcellulose.

9. An enteric coated tablet according to claims 1, 2, 3, 4, 5, 6, 7 or 8 wherein said (a) said undercoat layer, when present comprises from about 0% to about 3% by weight based on the total weight of said enteric coated tablet,
(b) said enteric coat layer comprises from about 4% to about 6% by weight based on the total weight of said enteric coated tablets, and
(c) said overcoat layer comprises from about 1% to about 3% by weight based on the total weight of said enteric coated tablet.

10. A process for preparing an enteric coated tablet which comprises applying to a tablet core containing aspirin as an active ingredient an undercoat layer comprising a non-enteric water soluble or water dispersible film forming polymer to form an under-coated aspirin containing tablet core, applying to said under-coated tablet core an intermediate enteric coat layer encompassing said under-coated tablet core and then applying an overcoat layer encompassing said enteric coat layer, said enteric coat layer comprising a water soluble or water dispersible film forming enteric polymer and said overcoat layer comprising a non-enteric water soluble on water dispersible film forming polymer.

11. A process according to claim 10 wherein said resulting tablet can withstand agitation in a basket at 100 rpm in artificial gastric juice having a pH of 1.2 at a temperature of 37° C. releasing less than 10% aspirin in two hours while dissolving not less than 85% aspirin in 90 minutes in artificial intestinal fluid having a pH of 6.8 at a temperature of 37° C.

12. A process according to claim 11 wherein said water soluble or water dispersible film forming enteric polymer is an acrylic resin.

13. A process according to claim 12 wherein said water soluble or water dispersible film forming enteric polymer is a copolymer that is anionic in character and based on polymethylacrylic acid and acrylic acid esters.

14. A process according to claim 13 wherein said film forming enteric polymer is of the formula

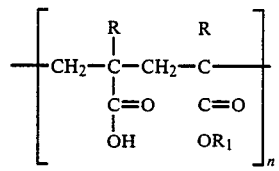

wherein n is a whole number,
R is H or $CH_3$ and $R_1$ is $CH_3$ or $C_2H_5$, the ratio of free carboxyl groups to ester groups being about 1:1 and the mean molecular weight of said polymer being about 250,000.

15. A process according to claim 14 wherein the said water soluble or water dispersible non-enteric polymer of said overcoat layer and said undercoat layer are the same or different and is one of the following polymers: hydroxypropylmethylcellulose, polyvinylpyrrolidone, hydroxypropylcellulose, polyethyleneglycol, methylcellulose, or pseudoethylcellulose.

16. A process according to claims 10, 11, 12, 13, 14, or 15 wherein
(a) said undercoat layer when deposited comprises from about 2% to about 3% by weight based on the total weight of said enteric coated tablet,
(b) said enteric coat layer comprises from about 4% to about 6% by weight based on the total weight of said enteric coated tablets, and
(c) said overcoat layer comprises from about 2% to about 3% by weight based on the total weight of said enteric coated tablet.

* * * * *